United States Patent [19]

Thaning

[11] Patent Number: 6,013,810

[45] Date of Patent: Jan. 11, 2000

[54] FREE RADICALS

[75] Inventor: Mikkel Thaning, Tygelsjö, Sweden

[73] Assignee: Nycomed Imaging AS, Oslo, Norway

[21] Appl. No.: 08/882,147

[22] Filed: Jun. 25, 1997

[30] Foreign Application Priority Data

Mar. 6, 1997 [GB] United Kingdom .................. 9704669

[51] Int. Cl.[7] .................. C07D 339/06; A61K 49/00
[52] U.S. Cl. .................................. 549/31; 424/9.3
[58] Field of Search ................... 424/9.3; 549/31

[56] References Cited

U.S. PATENT DOCUMENTS 5,530,140  6/1996  Andersson et al. ....................... 549/31
5,599,522  2/1997  Jørgensen et al. ..................... 424/9.33
5,728,370  3/1998  Andersson et al. ...................... 424/9.3

FOREIGN PATENT DOCUMENTS

WO 91/12024  8/1991  WIPO .

*Primary Examiner*—Richard L. Raymond
*Assistant Examiner*—Deepak R. Rao
*Attorney, Agent, or Firm*—Bacon & Thomas

[57] ABSTRACT

Novel triarylmethyl free radicals, their use as image enhancing agents in MRI, in particular to their use in Overhauser enhanced MRI of a sample for determining oxygen concentration of said sample.

3 Claims, 1 Drawing Sheet

FREE RADICALS

BACKGROUND OF THE INVENTION

The present invention relates to novel triarylmethyl free radicals and their use as image enhancing agents in magnetic resonance imaging (MRI), in particular to their use in electron spin resonance enhanced magnetic resonance imaging (OMRI) of a sample (for example a human or animal body) for determining the oxygen concentration of said sample.

MRI is a diagnostic technique that has become particularly attractive to physicians as it is non-invasive and does not involve exposing the patient under study to potentially harmful radiation (eg. X-rays). The technique, however, suffers from inter alia the problem of achieving effective contrast in the magnetic resonance (MR) images between tissue types having the same or closely similar imaging parameters.

Electron spin resonance enhanced MRI, referred to herein as OMRI(Overhauser MRI) but also referred to in earlier publications as ESREMRI or PEDRI, is a particular form of MRI in which enhancement of the magnetic resonance signals from which the images are generated is achieved by virtue of the dynamic nuclear polarization (the Overhauser effect) that occurs on VHF stimulation of an esr transition in a paramagnetic material, generally a persistent free radical, in the subject under study. Magnetic resonance signal enhancement may be by a factor of a hundred or more thus allowing OMRI images to be generated rapidly and with relatively low primary magnetic fields.

OMRI techniques have been described by several authors, notably Leunbach, Lurie, Ettinger, Grücker, Ehnholm and Sepponen, for example in EP-A-296833, EP-A-361551, WO-A-90/13047, J. Mag. Reson. 76:366–370(1988), EP-A-302742, SMRM 9:619(1990), SMRM 6:24(1987), SMRM 7:1094(1988), SMRM 8:329(1989), U.S. Pat. No. 4,719,425, SMRM 8:816(1989), Mag. Reson. Med. 14:140–147 (1990), SMRM 9:617(1990), SMRM 9:612(1990), SMRM 9:121(1990), GB-A-2227095, DE-A-4042212 and GP-A-2220269.

In the basic OMRI technique, the imaging sequence involves initially irradiating a subject placed in a uniform magnetic field (the primary field $B_0$) with radiation, usually VHF radiation, of a frequency selected to excite a narrow linewidth esr transition in a paramagnetic enhancement agent (hereinafter "an OMRI contrast agent") which is in or has been administered to the subject. Dynamic nuclear polarization results in an increase in the population difference between the excited and ground nuclear spin states of the imaging nuclei, i.e. those nuclei, generally protons, which are responsible for the magnetic resonance signals. Since MR signal intensity is proportional to this population difference, the subsequent stages of each imaging sequence, performed essentially as in conventional MRI techniques, result in larger amplitude MR signals being detected and more effective contrast.

A number of oxygen free radicals that is to say radicals where the unpaired electron or electrons are associated with the oxygen atom have been proposed as OMRI contrast agents including for example nitroxide stable free radicals, chloranil semiquinone radical and Fremy's salt (U.S. Pat. No. 4,984,573) and deuterated stable free radicals, in particular deuterated nitroxide stable free radicals (WO-A-90/00904).

In WO-A-91/12024, Nycomed Innovation AB proposed persistant carbon free radicals, i.e. radicals (e.g. triarylmethyl radicals) in which the unpaired electron(s) are primarily associated with carbon atoms, for use as OMRI contrast agents.

In WO-A-96/39367, Nycomed Imaging AS proposed various sulphur-based triarylmethyl radicals for use as OMRI contrast agents.

In any OMRI experiment under ambient conditions, paramagnetic oxygen will have a finite effect on the spin system present. Generally speaking, this may be dismissed as a secondary effect when compared to the primary interaction of the radical electron spin and the nuclear spin system. Nonetheless, it has been proposed that this effect may be used to determine oxygen concentration within a sample. Research has concentrated particularly on the use of nitroxide spin labels; radicals which suffer the inherent disadvantage of having broad linewidth esr resonances and therefore low sensitivity to the effects of oxygen. Thus, to date, the effect of oxygen has been recognised only in a qualitative sense and any attempt to attach a quantitative significance to the oxygen effect has failed. Moreover, in general, non-invasive techniques for oxygen determination have been slow to develop and typically are not suited to the study of tissues lying deep beneath the surface of a sample.

For example, Grücker et al (MRM, 34:219–225(1995)) reported a method for calculating oxygen concentration by measuring the Overhauser effect attributable to a nitroxide radical and relating the non-linear effect of oxygen on the Overhauser Factor to its concentration. This involved taking two images, one on-resonance and one off-resonance, and using a first order approximation to arrive at the oxygen concentration. However, Grücker observed that the correlation between actual and calculated oxygen concentration was poor and therefore that the method was inherently inaccurate. This was attributed to the large number of parameters involved in the calculation.

Ehnholm (U.S. Pat. No. 5,289,125) proposed an OMRI technique in which signals from a paramagnetic material were detected under at least two different sets of operating parameters whereby to generate images of various physical, chemical or biological parameters. While oxygen tension was one of several such parameters, Ehnholm did not demonstrate the use of the technique to quantitate dissolved oxygen.

SUMMARY OF THE INVENTION

It has now been found that certain novel sulphur based triarylmethyl radicals have advantageous properties for example an improved metabolism pattern which makes them particularly suitable for use as OMRI contrast agents.

DETAILED DESCRIPTION OF THE INVENTION

Figure 1:
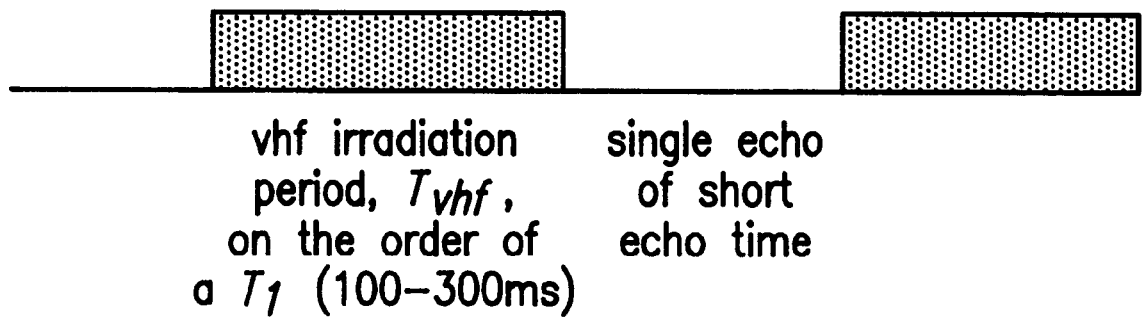
FIG. 1 is a typical OMRI imaging sequence used in the method of the invention.

Viewed from one aspect the present invention provides a radical compound of formula I

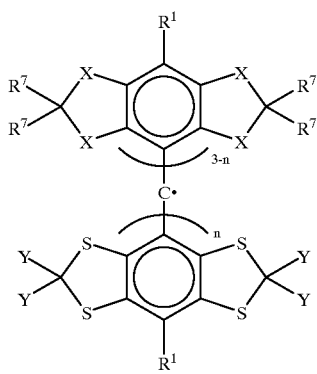

(wherein:
each X which may be the same or different represents an oxygen or sulphur atom or a group CO or $S(O)_m$ (where m is 1 to 3);
each $R^1$ which may be the same or different represents a hydrogen atom or group of formula —M, —XM, —X—$Ar^2$ or —$Ar^2$;
M represents a water solubilising group;
$Ar^2$ represents a 5–10 membered aromatic ring optionally substituted by a water solubilising group M;
each $R^7$ which may be the same or different represents a hydrogen atom, or a hydrocarbon group such as an alkyl, hydroxyalkyl, alkoxyalkyl, alkoxycarbonyl, or carbamoyl group, or a water solubilising group M or two groups $R^7$ together with the atom to which they are bound represent a carbonyl group or a 5 to 8 membered cycloalkylidene, mono- or di-oxacycloalkylidene, mono- or di-azacycloalkylidene or mono- or di-thiacycloalkylidene group optionally with the ring attachment carbon replaced by a silicon atom (preferably however in any spiro structure the ring linking atom will be bonded to no more than three heteroatoms) and $R^7$ where it is other than hydrogen, is optionally substituted by a hydroxyl group, an optionally alkoxylated, optionally hydroxylated acyloxy or alkyl group or a water solubilising group M;
n denotes 1, 2 or 3; and
each group Y which may be the same or different denotes any of the groups defined for $R^7$ hereinbefore with the proviso that at least one group Y is a hydroxylated $C_{2-6}$-alkyl group, preferably a $CH_2CH_2OH$ group) or a deuterated analog, precursor or salt thereof.

This definition covers radical precursors which may conveniently undergo a radical generation step shortly before administration or even in situ to produce the desired free radical. Radical precursors and radical generation steps are well-known to those skilled in the art.

Preferred radical compounds according to the invention include those of formula I wherein n is at least two and more preferably is three. Especially preferably, the group Y is in each case a hydroxylated $C_{2-6}$-alkyl group, more especially preferably a hydroxylated $C_{2-4}$-alkyl group, most especially a $CH_2CH_2OH$ group.

In the radical compounds according to the invention, the solubilising groups M may be any of the solubilising groups conventionally used in diagnostic and pharmaceutical products. Particularly preferred solubilizing groups M include optionally hydroxylated, optionally alkoxylated alkyl or oxo-alkyl groups and groups of formulae $R^5$, $COOR^5$, $OCOR^5$, CHO, CN, $CH_2S(O)R^5$, $CONR^5_2$, $NR^5COR^5$, $NR^5_2$, $SO_2NR^5_2$, $OR^5$, $PO_3^{2-}$, $SOR^5$, $SO_2R^5$, $SO_3M^1$, $COOM^1$ (where $R^5$ represents a hydrogen atom or an optionally hydroxylated, optionally aminated, optionally alkoxylated, optionally carboxylated alkyl, oxo-alkyl, alkenyl or alkaryl group and $M^1$ is one equivalent of a physiologically tolerable cation, for example an alkali or alkaline earth metal cation, an ammonium ion or an organic amine cation, for example a meglumine ion), —$(O(CH_2)_n)_mOR^5$ (where n is an integer having a value of from 1 to 3 and m is an integer having a value of from 1 to 5), —$CX(CHR^5)_nX$ or $CH_2R^8$ (where $R^8$ is a hydrophilic $R^5$ group) or $SR^{10}$ or $SO_2R^{10}$ where $R^{10}$ is a group $R^5$ or an alkyl group optionally substituted by one or more, especially two or three groups $COOR^5$, $OCOR^5$, CHO, CN, $CONR^5_2$, $NR^5COR^5$, $NR^5_2$, $SO_2NR^5_2$, $OR^5$, $PO_3^{2-}$, $SOR^5$, $SO_2R^5$, $SO_3M^1$, $COOM^1$, or —$(O(CH_2)_n)_mOR^5$.

Especially preferred as solubilizing groups M are groups of formula $C(H)_{3-n}(CH_2OH)_n$, $R^9$, $COR^9$, $SR^9$, $SOR^9$, $SO_2R^9$, $CON(R^9)_2$, $NR^9_2$, $NHR^9$ and $CONHR^9$ [where $R^9$ may represent a hydroxylated alkyl group such as a group

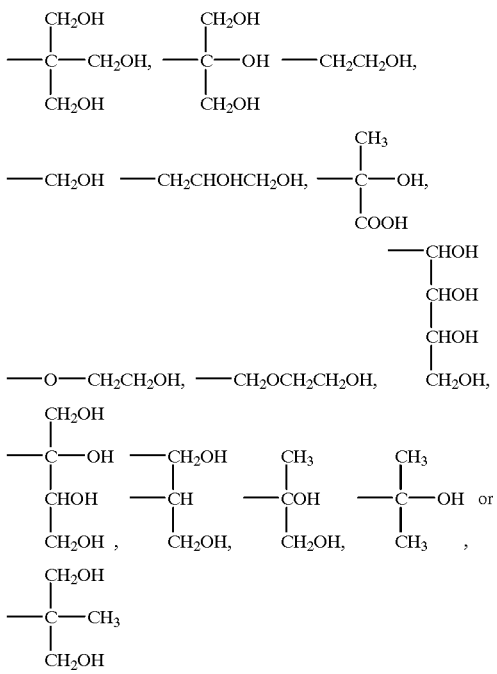

(although any $R^9$ group attached to a sulphur, nitrogen or oxygen atom is preferably not hydroxylated at the a carbon)] and groups of formula $SO_2R^{12}$ or $SR^{12}$ where $R^{12}$ is a group $CH_2COOR^3$, $CH(COOR^{13})_2$, $CH_2CONHR^9$, $CH_2CONR^9_2$, $CR^5(COOR^{13})_2$, $CH(CN)CO_2R^{13}$, $(CH_2)_nSO_3^-M^1$, $(CH_2)_nCOR^{13}$, $CH(COR^9)CH_2COR^9$ and $CH(R^5)COR^9$ where n, $M^1$ and $R^5$ are as hereinbefore defined and $R^{13}$ is a hydrogen atom, an alkyl group or a group $M^1$ or $R^9$.

In the radical compounds according to the invention, unless otherwise stated, any alkyl or alkenyl moiety preferably contains up to 6, especially preferably up to 4, carbon atoms.

In the radical compounds according to the invention, X is preferably selected from oxygen or sulphur atoms or $SO_2$ groups. Preferably two and especially preferably all four X groups are identical, especially preferably they are all sulphur atoms.

In the radical compounds according to the invention preferred identities for the group $R^1$ may be selected from the group consisting of —H, —$SCH_2COO^-Na^+$, —$SO_2R^2$, —$SR^2$, —$SCH_2COOCH_2CH_3$, —$SO_2C(R^2)_2$ $CH_2CHOHCH_2OH$, —$SO_2NR^2_2$, —$SO_2CH_2CON(R^2)_2$, —C—(CH$_2$CH$_2$OH)$_3$, —SO$_2$—C(H) (COOCH$_2$CH$_3$)$_2$,
—CH$_2$CON(CH$_2$CH$_2$OH)$_2$, —COOH, —CO$_2$Me,
—CO$_2$Et, —CO$_2$M$^1$—SO$_2$—C— (CH$_2$CH$_2$OH)$_2$
  COOCH$_2$CH$_3$,
—SO$_2$C— (CH$_2$CH$_2$OH)$_2$
  CH$_2$OH,
(where M$^1$ is as hereinbefore defined and R$^2$ is H or optionally hydroxylated alkyl eg. CH$_2$CH$_2$OH, CH$_2$CHOHCH$_2$OH, CH$_3$, CH$_2$CH$_3$, CH$_2$(CHOH)$_4$CH$_2$OH) or deuterated analogues thereof.

The most preferred compound according to the invention is

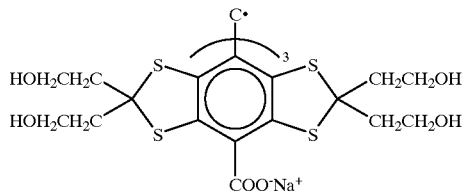

Compounds according to the invention have been found to have an improved metabolism pattern, namely a half-life which is typically greater than 30 minutes when a dose of 0.05 mmol/kg is injected into a rat (where the half-life is defined as the time from injection until the radical concentration in the blood equates with the metabolite concentration).

Further aspects of the invention provide the use of a radical compound according to the invention for the manufacture of a contrast medium for use in OMRI and a method of magnetic resonance investigation of a sample, said method comprising introducing into said sample a radical compound according to the invention, exposing said sample to a first radiation of a frequency selected to excite electron spin transitions in said radical, exposing said sample to a second radiation of a frequency selected to excite nuclear spin transitions in selected nuclei (eg. protons) in said sample, detecting free induction decay signals from said sample, and, optionally, generating an image or dynamic flow data from said detected signals.

Viewed from a still further aspect, the invention provides a magnetic resonance imaging contrast medium composition comprising a radical compound according to the invention together with at least one pharmacologically acceptable carrier or excipient.

For in vivo imaging, the radical compound should preferably be a physiologically tolerable radical, or one presented in a physiologically tolerable, e.g. encapsulated, form.

For the method according to the invention the preferred radicals are those which have relatively few transitions, e.g. less than 15, preferably less than 10, in their ESR spectra and radicals having narrow linewidth ESR transitions, e.g. up to 500 mG, preferably less than 150 mG, especially less than 60 mG and particularly less than 25 mG, are especially preferred (The linewidths referred to are conveniently the intrinsic linewidths (full width at half maximum in the absorption spectrum) under ambient conditions).

Whilst low numbers of ESR transition lines are generally preferred to obtain more effective coupling of the ESR and NMR transitions, good coupling (and therefore enhancement of the MR signal) may also be achieved with radicals showing a large number of ESR transitions.

Where the radicals have a multiplicity of ESR transitions, the hyperfine splitting constant is preferably very small. In this connection radicals having as few as possible non-zero spin nuclei, positioned as far away as possible from the paramagnetic centre are thus especially preferred.

The radical compounds according to the invention may be coupled to further molecules for example to lipophilic moieties such as long chain fatty acids or to macromolecules, such as polymers, proteins, polysaccharides (e.g. dextrana), polypeptides and polyethyleneimines. The macromolecule may be a tissue-specific biomolecule such as an antibody or a backbone polymer such as polylysine capable of carrying a number of independent radical groups which may itself be attached to a further macromolecule. Coupling to lipophilic molecules or substitution of the radical with lipophilic groups is particularly useful since it may enhance the relaxivity of the radicals in certain systems such as blood. Such lipophilic and macromolecular derivatives of the radical compound of formula I and salts thereof form a further aspect of the present invention.

The linkage of a compound according to the invention to the further molecule may be effected by any of the conventional methods such as the carbodiimide method, the mixed anhydride procedure of Krejcarek et al. (see Biochemical and Biophysical Research Communications 77: 581 (1977)), the cyclic anhydride method of Hnatowich et al. (see Science 220: 613 (1983) and elsewhere), the backbone conjugation techniques of Meares et al. (see Anal. Biochem. 142: 68 (1984) and elsewhere) and Schering (see EP-A-331616 (Deutsch/Schering) for example) and by the use of linker molecules as described for in U.S. Pat. No. 5,208,324 (Klaveness/Nycomed).

In view of their beneficial properties, one further aspect of the present invention is the use of the radical compounds of the invention as conventional OMRI contrast agents, as ESR contrast agents or as ESR spin labels in ESR imaging or in magnetometry.

The radical compounds according to the invention have been found to be useful in providing a non-invasive method based on OMRI for determining the oxygen concentration of a sample (hereinafter the OXI method) which involves manipulation of the Overhauser effect attributable to the radical compounds of the invention. More specifically, the method is based on observing and manipulating the varying enhancement of a proton signal due to the changed saturation characteristics of the radical in the presence of oxygen.

Viewed from a yet further aspect the present invention provides a method of determining oxygen concentration in a sample, for example a human or non-human, preferably mammalian, subject, said method comprising the following steps:

introducing into said sample an effective amount of a physiologically tolerable radical compound according to the invention, preferably a radical having an esr transition with a linewidth (measured in water at 37° C.) of less than 400 mG, more preferably less than 150 mG;

irradiating said sample with radiation of an amplitude (i.e. power) and frequency selected to stimulate an electron spin resonance transition of said radical;

detecting electron spin resonance enhanced magnetic resonance signals from said sample under at least first, second and third conditions, whereby under said first and second conditions said radiation is of a first frequency, under said third conditions said radiation is of a second frequency different from said first frequency, under said first, second and third conditions said radiation is of a first, second and third amplitude, said first and second amplitudes at least being different from each other; and manipulating said detected signals whereby to determine oxygen concentration in said sample.

In a preferred embodiment, the OXI method comprises:

(a) introducing a radical compound according to the invention, e.g. parenterally, for example by injection into body tissue or into the vasculature;

(b) generating a first OMRI image of said sample at VHF power $P_A$, irradiation period $T_{VHF1}$ and on-resonance ($\Delta H=o$) (i.e. where the frequency of the radiation is selected to be the resonance frequency of the esr transition);

(c) generating a second OMRI image of said sample at a second VHF power $P_B$, irradiation time $T_{VHF1}$ and on-resonance ($\Delta H=O$);

(d) generating a third OMRI image of said sample at VHF power $P_C$ (eg equal to $P_A$ or $P_B$), irradiation time $T_{VHF1}$ and off-resonance ($\Delta H \neq O$, for example 100–200 mG);

(e) manipulating the images obtained in steps (b) to (d) and calibrating using parameters determined ex vivo to provide an oxygen image of said sample.

In an especially preferred embodiment, a fourth and fifth OMRI image are additionally generated in the imaging sequence. The conditions for the fourth image are identical to the first image but the VHF irradiation time $T_{VHF2}$ is different (for example twice as long, i.e. $T_{VHF2}=2T_{VHF1}$) and the fifth image is obtained without VHF irradiation, eg. is a native image of intensity $I_0$, generated by conventional MRI with a repetition time $T_R=T_{VHF}$.

In a further embodiment, a native image (i.e. one obtained by conventional MRI) of the sample (e.g. body) may be generated to provide structural (e.g. anatomical) information upon which the oxygen image may be superimposed. In this way, precise location of, for example, an oxygen deficient tumour will be possible.

Accurate measurement of the level of oxygen in bodily tissues is an invaluable aid to the clinician and the OXI method has a variety of end uses. For example, knowledge of the concentration of oxygen dissolved in blood can be used (through known rate constants) to calculate the concentration of oxygen associated with haemoglobin. This is a useful parameter which is presently measured either by undesirable invasive techniques or using the BOLD MR imaging technique which involves high field imaging to determine the effect of oxygen on paramagnetic iron but which has the disadvantage that to determine blood oxygen concentration the volume of blood in which the measurement was made needs to be known.

Other uses of the OXI method will be readily apparent to the skilled person and include oxygen imaging (e.g. mapping) of, for example, the heart and arteries and of malignant tumours, for example in the brain, breast, lung, lymphoid tissues and superficial areas of the liver. In the case of oxygen imaging of tumours, success in treatment of malignant tumours by radiotherapy may be reflected in the level of oxygen in the tissue (typically an oxygen concentration of less than 0.01 mM will indicate that the tissue is necrotic and thus that treatment is likely to be ineffective).

It will also be apparent that the OXI method will be useful in cardiology, surgery and intensive care where levels of oxygen and even perfusion can be non-invasively assessed in almost any tissue.

The manipulation of the detected MR signals in the OXI method will generally be to generate an image data set (i.e. a data set from which an image may be generated) indicative of radical concentration and one or more image data sets indicative of radical electron relaxation times (generally $T_{1e}$, $T_{2e}$ or $T_{1e}-T_{2e}$) and manipulation of these data sets and calibration with ex vivo calibration data to yield an image data set indicative of oxygen concentration. This oxygen concentration image data set can be transformed into an oxygen concentration image or can be subject to an upper or lower limit filter to identify regions of high or low oxygen concentration, which can again if desired be displayed as an image.

Broadly speaking, the Overhauser enhancement of the proton MR signal is dependent on the relaxation times $T_{1e}$ and $T_{2e}$ of the esr transition of the radical used in the OXI method. These relaxation times themselves are dependent on the concentrations of the radical and dissolved oxygen in the body fluid as well as on the temperature and chemical nature of the body fluid. However while the Overhauser enhancement can easily be used to determine the oxygen concentration for an isolated small volume sample of known radical concentration ex vivo, the determination of oxygen concentration in vivo is complicated since the Overhauser enhancement is also strongly dependent on the sample structure for a large non-isolated sample, such as a living body, due inter alia to non-uniform radiation penetration into the large sample.

Thus although the OXI method requires calibration data, obtained for a range of radical and oxygen concentrations in a fluid sample (e.g. blood) which corresponds to the body fluid in which oxygenation is to be determined and at a pre-set temperature (e.g 37° C.), further data manipulation is required in order to extract the in vivo oxygen concentrations from the OMRI signals detected for the sample.

The calibration data are generated ex vivo by determining Overhauser enhancement values for the radical in the selected body fluid, at the selected temperature and at a range of oxygen (and preferably also radical) concentrations. The intrinsic esr relaxation times for the radical can be determined, under the same conditions, using a conventional esr spectrometer equipped with a temperature controller, with the oxygen concentration being determined using a method known to produce accurate and reproducible results (see Ravin et al J. Appl. Physiol. 18:784–790 (1964)).

In general, radical concentrations up to 0.2, preferably up to 1.0, especially up to 1.5 mM, and oxygen concentrations of up to 0.1, preferably up to 0.5 mM should be investigated to generate the calibration data.

Calibration of a blood sample at 37° can be used to determine maximum Overhauser enhancement (ie. at infinite VHF power and infinite radical concentration and $T_1$. Equations which relate $T_{1e}$ and $T_{2e}$ to the radical and oxygen concentration by a linear relationship can be derived experimentally for whatever radical is used in the method of the invention. The equations are:

$$2\left(\sqrt{3}\,\gamma_e T_{2e}\right)^{-1} = x + yC_{rad} + zC_{o2} \qquad (1)$$

$$2\left(\sqrt{3}\,\gamma_e T_{1e}\right)^{-1} = a + bC_{rad} + cC_{o2} \qquad (2)$$

$$\left(\gamma_e \sqrt{T_{1e} T_{2e}}\right)^{-1} = h + jC_{rad} + kC_{o2} \qquad (3)$$

where x, y, z, a, b, c, h, j and k (in mG) are the experimentally determinable coefficients characteristic of the chosen radical $\gamma_e$ is the electron gyromagnetic ratio, $C_{rad}$ is the radical concentration (mM), $C_{O2}$ is the oxygen concentration (mM), $T_{1e}$ and $T_{2e}$ are electron relaxation time(s).

With this calibration data, if $T_{1e}$, $T_{2e}$ or $T_{1e}-T_{2e}$ are calculated for a pixel in the sample's OMRI image then equations (1), (2) or (3) can easily be used to determine the oxygen concentration for that pixel. The radical concentration can be determined by manipulation of the MR signals detected in the OXI method whereby to generate a radical concentration image data set.

However, the $T_{1e}$, $T_{2e}$ or $T_{1e}$–$T_{2e}$ values for the pixel must be extracted from the OMRI signals detected in the imaging procedure. The OMRI imaging sequence used in the OXI method may be any one of the conventional sequences. An example of one such usable sequence is shown schematically in FIG. 1. This sequence involves a VHF irradiation period ($T_{VHF}$) of approximately the same magnitude as $T_1$ for the water proton, and a single echo of time TE much less than $T_2$. Pixel intensity (I) is then given by equation (4):

$$I \alpha (1-\exp(-T_{VHF}/T_1)) \quad (4)$$

During VHF irradiation, dynamic proton polarization $<I_z>$ occurs The steady state is governed by the Overhauser equation (5)

$$\frac{\langle I_z \rangle}{I_0} = 1 - \left[ \frac{S_0}{I_0} k \cdot f \cdot \frac{S_0 - \langle S_z \rangle}{S_0} \right] \quad (5)$$

where $S_0/I_0$ is equal to 658 for an electron: proton dynamic nuclear polarization (I, here represents the equilibrium magnetisation), k is the coupling factor (equal to ½ at low field), f is the leakage factor, and $(S_0-<S_z>)/S_0$ is the degree of saturation (SAT) of the electron spin transition).

The leakage factor f is given by equation (6)

$$f = \frac{rC_{rad}T_{10}}{1 + rC_{rad}T_{10}} = rC_{rad}T_1 \quad (6)$$

(where r is the relaxivity of the radical;

$C_{rad}$ is the radical concentration, and $T_{10}$ is the proton relaxation time $T_1$ in the absence of the radical).

The pixel intensity of the final image is given by equation (7)

$$I \alpha (1-\exp(-T_{VHF}/T_1)) (1-329 r C_{rad} T_1 SAT) I_0 \quad (7)$$

(where $I_0$ is the intensity of the native image pixel).

As can be seen from a Taylorian expansion of the exponential function in equation (7), provided that $T_{VHF}$ is significantly less than $T_{10}$, $T_1$ disappears to a first order. SAT depends on the strength of the exciting VHF field $B_{10}$ and obeys the basic Bloch equations. Where the esr transition is a single Lorentzian this means that SAT is given by equation (8)

$$SAT = \frac{\alpha P \gamma_e^2 T_{1e} T_{2e}}{1 + \alpha P \gamma_e^2 T_{1e} T_{2e} + (\Delta \omega T_{2e})^2} \quad (8)$$

(where $\alpha$ is a conversion factor;

P is the VHF power; and $\Delta \omega$ is the distance from resonance of the off-resonance VHF excitation frequency (where an on-resonance frequency is used, $\Delta \omega$ is of course zero)).

The conversion factor $\alpha$ is strongly spatially variant in in vivo large sample images, and thus knowledge of P, SAT, $\gamma_e$ and $\Delta \omega$ is not in itself sufficient to enable oxygen concentration to be determined.

In most cases, moreover, the ear transition will not be a single Lorentzian due to residual magnetic couplings within the radical molecule. Where, as in the case with narrow esr linewidth radicals such as the trityls mentioned herein, the coupling constants are much smaller than the linewidth, the resonance lineshape will become a Voigt function and SAT will be the integral of all off-resonance values weighted by a Gaussian intensity function as in equation (9)

$$SAT = 1 - \sqrt{\frac{2}{\pi}} \frac{1}{\Delta H_{pp}^G} \int_{-\infty}^{\infty} \exp(-2H'^2 / \Delta H_{pp}^{G\,2}) \quad (9)$$

$$\frac{1 + \frac{4}{3}(\Delta H - H')^2 / \Delta H_{pp}^{L\,2}}{1 + \frac{4}{3}(\Delta H - H')^2 / \Delta H_{pp}^{L\,2} + \frac{2}{\sqrt{3}} \alpha P \gamma_e T_{1e} / \Delta H_{pp}^L} dH'$$

(where $\Delta H_{PP}^G$ and $\Delta H_{PP}^L$ are the first derivative peak-to-linewidth of the Gaussian and Lorentzian functions and in field units $\Delta H$ is the off-resonance field).

Equations (8) and (9) apply to single esr peaks homogeneously or in homogeneously broadened respectively. For well separated peaks, with large couplings, the saturation degree will be reduced by a factor corresponding to the far-off-resonance fraction.

In the OXI method, the data manipulation will in general be to fit SAT as determined on a pixel-by-pixel basis to one of equations (8) or (9) and thereby extract $T_{1e}$, $T_{2e}$ or $T_{1e}$–$T_{2e}$, again on a pixel-by-pixel basis so permitting pixel oxygen concentration to be calculated from the experimentally determined equations (1), (2) and (3).

In one preferred embodiment of the method of the invention, data manipulation is-effected to calculate esr linewidth based on inhomogeneous broadening (equation (9)).

At its most elementary level, this method requires three OMRI images to be generated. These however can be, and preferably are, supplemented with further images recorded off-resonance, and also preferably are supplemented by images recorded with different irradiation times and native images.

In the elementary version of the method images A, B and C are recorded as follows:

A: VHF power $P_A$. $\Delta \omega = 0$ (i.e. on-resonance) $\Delta H = O$. Irradiation time $T_{VHF} = T_{VHF1}$ B: VHF power $P_B$ ($\neq P_A$). $\Delta \omega = 0$. Irradiation time $T_{VHF} = T_{VHF1}$ C: VHF power $P_C$ (e.g.=$P_A$ or =$P_B$) $\Delta \omega \neq 0$ (i.e. off-resonance) $\Delta H \neq O$ (e.g. 100–200 mG). Irradiation time $T_{VHF} = T_{VHF1}$ Under these conditions, pixel intensity can be written as;

$$I = A \left\{ 1 - \sqrt{\frac{2}{\pi}} \frac{1}{\Delta H_{pp}^G} \int_{-\infty}^{\infty} \exp(-2H'^2 / \Delta H_{pp}^{G\,2}) \right. \quad (10)$$

-continued $$\left. \frac{1 + \frac{4}{3}(\Delta H - H')^2 / \Delta H_{pp}^{L\,2}}{1 + \frac{4}{3}(\Delta H - H')^2 / \Delta H_{pp}^{L\,2} + \frac{2}{\sqrt{3}}\alpha P\gamma_e T_{1e} / \Delta H_{pp}^L} dH' \right\} - B$$

(where
A=Gain x proton density×r$C_{rad}T_1$×(1-exp($-T_{VHF}/T_1$)) for r$C_{rad}T_1$>>1
(Gain is the system gain factor and proton density is the proton density of the pixel);
and B=Gain×proton density×(1-exp($-T_{VHF}/T_1$)).

Equation 10 contains five unknowns :$T_1$, proton density, $C_{rad}$, $\Delta H_{PP}^L = 2/\sqrt{3}\gamma_e \cdot T_{2e}$ and $\alpha T_{1e}$.

With a large enhancement (e.g. about 10), short $T_{VHF1}$ relative to $T_1$ and essentially uniform proton density in the fluid medium in which the radical is distributed, B can be omitted and the three unknowns $C_{rad}$, $\Delta H_{PP}^L$ and $\alpha T_{1e}$ can be fitted on a pixel-by-pixel basis from the three values of I obtained from images A, B and C respectively. Radical concentration ($C_{rad}$) can then be determined by scaling A with Gain and r to yield a radical concentration image. Using the determined value of $\Delta_{PP}^L$ and the radical concentration image, the pp oxygen concentration image can then be calculated from equation (1).

A more accurate determination of oxygen concentration can be made using this method if two further images are generated, one image D on-resonance, at power $P_A$ and at irradiation time $T_{VHF}=T_{VHF2}$ (where $T_{VHF2} \neq T_{VHF1}$, e.g. $T_{VHF2}=2\times T_{VHF1}$), and the second image E without VHF stimulation, using conventional MR with repetition time TR=$T_{VHF1}$. Image E gives the native intensity $I_0$ for the pixels.

From the five values for pixel intensity all five unknowns can be calculated, again yielding a concentration image an $_{PP}\Delta H^L$ from which an oxygen concentration image can be determined using equation (1).

In this method, if reference samples containing body fluid and radical, are disposed about the sample surface (e.g. tubes of blood containing the radical at known concentration), the oxygen concentration image can be adjusted to express concentration even more accurately.

A further preferred embodiment of the method takes advantage of the greater sensitivity to oxygen is concentration of equation (3), i.e. of the product $T_{1e}$-$T_{2e}$. This method however requires $\alpha$, which gives the VHF magnetic field at the pixel, to be determined.

In this further method, oxygen concentration and radical concentration images are calculated from three or more images as above, a $^{1/}T_{1e}$ image is calculated from these images and an $\alpha$-image is calculated by multiplying the $^{1/}T_{1e}$ image by $\Delta T_{1e}$ as determined. The $\alpha$-image is then smoothed using for example a polynomial function. It is preferred that reference samples be disposed about the sample under investigation as discussed above. If this is done then the smoothing of the $\alpha$ image can be achieved using a smoothing function with fixed values at the reference sample sites. This reduces statistical error in the images, is justified as the spatial variance of $\alpha$ is slow and, with fixed reference points, produces an accurate $\alpha$ image.

Using this $\alpha$-image, the product of $\Delta H^L_{PP}$ wand $^{1/}T_{1e}$ can be calculated and from this (which is dependent on $^{1/}T_{1e}$-$T_{2e}$) and the radical concentration image, a more precise oxygen image can be calculated.

If reference sample tubes are not used, then the smoothed $\alpha$-image can still be calculated but in this event the $\alpha$-values determined are preferably used in the calculation of the three (or five) variables from the detected OMRI images with a further smoothed $\alpha$-image being calculated from the resulting $^{1/}T_{1e}$ image and with the procedure being repeated until successively generated $\alpha$-images are essentially unchanged (i.e. the procedure converges to a best-fit).

Whilst for radicals having a large esr linewidth the Lorentzian model is an accurate approximation for the lineshape, in the case of narrow esr linewidth radicals more precise analysis of the lineshape is called for and leads to a more accurate determination of the oxygen concentration.

In allowing the spatial variation of the VHF magnetic field to be calculated, the further method described above yields an absolute quantification of the longitudinal relation time (or the product of the longitudinal and transverse relaxation time). The longitudinal relaxation time (and even more so the product of the longitudinal and transverse relaxation rates) is more sensitive to oxygen and so this method overall is the more sensitive technique.

Although the above described methods have focused on the use of voigt functions to calculate the various unknown parameters, the OXI method may equally involve the use of Lorentzian functions where these are an accurate model of the ear lineshape and such a method forms a further embodiment of the invention. For example, in large linewidth radicals the effects of inhomogeneity may be neglected and the lineshape will essentially be Lorentzian. Thus in this preferred embodiment, the data manipulation step will essentially amount to fitting SAT (as determined on a pixel-by-pixel basis) to equation (8), extracting $T_{1e}$, $T_{2e}$ and $T_{1e}$-$T_{2e}$ on a pixel-by-pixel basis thereby permitting oxygen concentration to be determined from empirical relationships such as equations (1), (2) and (3).

In practice, it may be necessary to compensate for flow effects in the method of the invention and the appropriate steps will be known to those skilled in the art. Other parameters such as for example sample viscosity, pH, temperature, radical self-broadening, etc. are typically only secondary effects and thus may be neglected when compared to the first order effects of paramagnetic oxygen in the method of the invention. Radical self-broadening is however corrected for in equations 1 to 3.

Generally speaking, for use in the OXI method it is preferred for the radical to be stable under physiological conditions with a sufficiently long half life (at least one minute, preferably at least 30 minutes) and a long electronic relaxation time and good relaxivity. It will be apparent from the discussion of the OXI method that the sensitivity of the oxygen measurement will be improved with radicals having narrow linewidth esr transitions, e.g. up to 500 mG, preferably less than 150 mG, especially less than 60 mG.

Preferably, the radical selected for use in the OXI method should distribute substantially into the extracellular fluid (i.e. should be an ECF agent) since the effects of paramagnetic iron (e.g. the iron within the red blood cells) may be avoided there.

Another preferred characteristic of the radical chosen for use in the OXI method is that they should have a low self-broadening effect, preferably less than 100 mG, especially preferably between 0 and 50 mG per mM of the radical itself.

The radical compounds according to the invention may be prepared from their non-radical precursor compounds by conventional radical generation methods. Suitable non-radical precursor compounds include the corresponding triaryl methanes, triaryl methyl halides and triaryl methanols, and derivatives, e.g. ethers, of the triaryl methanols.

In a further aspect the invention provides a process for the preparation of the radical compounds according to the invention which comprises subjecting a radical precursor therefor to a radical generation step and optionally subsequently modifying the substitution on the aryl moieties, e.g. by oxidation or reduction. By such modification for example sulphide substituents, (e.g. —$SCH_3$ or —$SCH_2COOEt$) may be oxidized to the corresponding sulphones so avoiding problems of acidic hydrogens prior to radical formulation. Similarly lipophilic substituents (such as —$SCH_2COOEt$) may be reduced to corresponding hydrophilic substituents (e.g. —$SCH_2CH_2OH$).

The radical-precursor conveniently contains a group displaceable to produce a radical eg. an OH, Hal, H, COOH, —COO.O.CO.C— or —C.NN.C— group. Methods for preparing radical compounds from these precursors are disclosed in inter alia WO-A-91/12024 and WO-A-96/39367.

The non-radical precursors may themselves be prepared by methods conventional in the art and a number of suitable methods are described in WO-A-91/12024 and WO-A-96/39367.

Radicals with long half lives in aqueous solution, for example at least one hour, preferably ten days, more preferably fifty days and especially preferably at least one year are particularly desirable for use in in vivo imaging.

For use in OMRI in general or the OXI method, the radical compounds according to the invention are physiologically tolerable or in a physiologically tolerable form (eg. in solution, encapsulated or as a precursor). Conveniently the compounds are formulated into contrast media together with conventional pharmaceutical carriers or excipients. Contrast media manufactured or used according to this invention may contain, besides the radical (or the non-radical precursor where radical formation is to be effected immediately before administration or in situ), formulation aids such as are conventional for therapeutic and diagnostic compositions in human or veterinary medicine. Thus the media may for example include solubilizing agents, emulsifiers, viscosity enhancers, buffers, etc. The media may be in forms suitable for parenteral (e.g. intravenous) or enteral (e.g. oral) application, for example for application directly into body cavities having external voidance ducts (such as the gastrointestinal tract, the bladder and the uterus), or for injection or infusion into the cardiovascular system. However solutions, suspensions and dispersions in physiological tolerable media will generally be preferred.

Radicals which are relatively unstable or insoluble in the sample environment may be encapsulated, e.g. in gastric juice resistant capsules containing a medium in which they are stable. Alternatively, the radical may be presented as an encapsulated freeze dried powder in a soluble capsule. Such formulations might conveniently be dissolved shortly before in vivo use.

For use in in vivo diagnostic imaging, the medium, which preferably will be substantially isotonic, may conveniently be administered at a concentration sufficient to yield a 1 micromolar to 10 mM concentration of the free radical in the imaging zone; however the precise concentration and dosage will of course depend upon a range of factors such as toxicity, the organ targetting ability of the contrast agent, and the administration route. The optimum concentration for the free radical represents a balance between various factors. In general, optimum concentrations would in most cases lie in the range 0.1 to 100 mm, especially 0–2 to 10 mM, more especially 0.5 to 5 mM. Compositions for intravenous administration would preferably contain the free radical in concentrations of 10 to 1000 mM especially 50 to 500 mM. For ionic materials, the concentration will particularly preferably be in the range 50 to 200 mM, especially 130 to 170 mM and for non-ionic materials 200 to 400 mM, especially 290 to 330 mM. For imaging of the urinary tract or the renal or biliary system however, compositions may perhaps be used having concentrations of for example 10 to 100 mM for ionic or 20 to 200 mM for non-ionic materials. Moreover for bolus injection the concentration may conveniently be 0.1 to 100 mM, preferably 5 to 25 mM, especially preferably 6 to 15 mM.

The present invention will now be further illustrated by the following non-limiting Examples (percentages, parts and ratios are by weight and temperatures are in degrees Celsius unless otherwise stated).

EXAMPLE 1

Benzo[1,2-d:4,5-d']bis(1,3)dithiole-2,2,6,6-tetracetic acid ethyl ester.

The reaction was performed in dry flask under argon atmosphere. 1,2,4,5-Benzotetrathiole (74 g, 0.359 mol) and diethylacetone dicarboxylate (195.5 ml, 1.076 mol) were mixed with dichloromethane (3500 ml) and the mixture was cooled to −10° C. Fluoroboric acid (197.7 ml, 1.434 mol) was added and the cooling bath was changed to an icebath. The mixture was stirred at 0° C. for 90 minutes and then poured into solid sodium carbonate (300 g) under vigorous stirring. The slurry was filtered and the filtrate was evaporated to dryness. The solid residue was triturated with heptane (2×250 ml) and dried in a stream of air.

Yield: 138.6 g (67%)

$^1$H NMR (CDCl$_3$) 6.97 (s, 2H), 4.16 (q, J=7.2 Hz, 8H) 3.49 (s, 8H) 1.26 (t, J=7.2 Hz, 12H).

EXAMPLE 2

2,2,6,6-Tetra(hydroxyethyl)benzo[1,2-d:4,5-d']bis(1,3) dithiole.

A dry flask under argon atmosphere was charged with diethyl ether (2600 ml) and LiAlH$_4$ (21.2 g 0.56 mol) Benzo[1,2-d:4,5-d']bis(1,3)dithiole-2,2,6,6-tetraacetic acid ethyl ester (80.2 g, 0.139 mol) was added and the mixture was refluxed for 26 h. The mixture was cooled to ambient temperature and ethanol (165 ml) was carefully added followed by water (410 ml). The ether was decanted off and the white precipitate was stirred with water (3300 ml) to give a slurry. After acidification with hydrochloric acid the slurry was filtered and the crude product was washed with water and dried.

Yield: 55.0 g (97%)

$^1$H NMR (DMSO-d$_6$): 7.19 (s, 2H), 4.64 (t, J=5.7 Hz, 4H) 3.56 (q, J=5.7 Hz, 8H), 2.22 (t, J=6.3 Hz)

EXAMPLE 3

2,2,6,6,-Tetra(t-butoxyethyl)benzo[1,2-d:4,5-d']bis(1,3) dithiole

A dry flask under argon was charged with 2,2,6,6-tetra (hydroxyethyl)benzo[1,2-d:4,5-d']bis(1,3)dithiole (50.3 g, 0.124 mol), tetrahydrofuran (1200 ml) and isobutene (300 ml). Trifluoromethane sulphonic acid (21.8 ml, 0.248 mol) was added over 1 minute and the mixture was stirred for 1 h. The reaction mixture was poured into solid sodium carbonate (750 g) under vigorous stirring. After filtration through a silica pad the filtrate was evaporated to dryness and the solid residue was recrystallized from ethanol to give white needles.

Yield: 61.6 g (79%).

$^1$H NMR (CDCl$_3$): 6.95 (s, 2H), 3.56 (t, J=6.6, 8H) 2.34 (t, J=6.6 Hz, 8H) 1.18 (s, 36H)

EXAMPLE 4

2,2,6,6-Tetra(t-butoxyethyl)4-iodo-benzo[1,2-d:4,5-d']bis(1,3) dithiole

A dry flask under argon was charged with 2,2,6,6-tetra(t-butoxyethyl)benzo[1,2-d:4,5-d']bis(1,3)dithiole (60.0 g, 95.08 mmol) and dry tetrahydroturan (2000 ml). The mixture was cooled to −20° C. and n-Butyl lithium (76 ml of a 2.5 M solution in hexane, 0.19 mol) was added over 3 minutes. The mixture was stirred for 20 minutes at −20° C. and then a solution of iodine (120 g, 0.475 mol) in tetrahydroturan (500 ml) was added. The reaction mixture was poured into an aqueous sodium bisulphite solution and extracted with diethyl ether. The organic phase was washed once with an aqueous solution of sodium bisulphite and once with brine, dried (MgSO$_4$) and evaporated.

The product was purified by chromatography on silica gel using a mixture of CH$_2$Cl$_2$ and ethyl acetate as the eluent.

Yield: 35.7 g (51%).

$^1$H NMR (CDCl$_3$): 6.87 (s, 1H), 3.57 (t, J=6.6 Hz, 8H) 2.35 (t, J=6.6 Hz 12 H)

EXAMPLE 5

Tris(2,2,6,6-tetra-(t-butoxy-ethyl)benzo[1,2-d:4,5-d']bis(1,3)dithiole-4-yl)methanol.

A dry flask under argon was charged with 2,2,6,6-tetra(t-butoxyethyl)4-iodo-benzo[1,2-d:4,5-d']bis(1,3)dithiole (29.0 g 38.3 mmol) and dry diethyl ether (520 ml). The mixture was cooled to −78° C. and n-butyl lithium (15.3 ml of a 2.5 M solution in hexane, 38.3 mmol) was added and the cooling bath was removed. After 30 minutes an etherial solution (0.319 M) of diethyl carbonate (40 ml, 12.76 mmol) was added dropwise over 120 minutes. Ten minutes after complete addition, the mixture was poured into aqueous NaH$_2$PO$_4$ and extracted with diethyl ether (2×250 ml). The organic phase was washed with water, dried (MgSO$_4$) and evaporated. The product was purified by chromatography on silica gel using a mixture of C$_2$Cl$_2$ and acetonitrile as the eluent.

Yield: 15.7 g (64%).

$^1$H NMR (CDCl$_3$): 7.07 (s, 3H), 6.57 (s, 1H), 3.30–3.60 (m, 24H), 2.10–2.50 (m, 24H), 1.12–1.17 (m, 108H).

EXAMPLE 6

Tris(8-hydroxycarbonyl-2,2,6,6-tetra-(t-butoxy-ethyl)benzo[1,2-d:4,5-D']bis(1,3)dithiole-4-yl)methanol A dry flask under argon atmosphere was charged with N,N,N',N'-tetramethylethylene diamine (12.5 ml) and tris(2,2,6,6-tetra-(t-butoxyethyl)benzo[1,2-d:4,5-d']bis(1,3)dithiole-4-yl)methanol (960 mg, 0.5 mmol). The mixture was cooled to −20° C. and n-butyl lithium (3.0 ml of a 2.5 M solution in hexane, 7.5 mmol) was added over 2 minutes. The mixture was allowed to reach ambient temperature and after 1 h the mixture was heated to 40° C. and kept at this temperature for 20 minutes. The mixture was then transferred to a dry flask containing an excess of carbon dioxide (s) and was then left to reach ambient temperature. The reaction mixture was taken up in water (200 ml) and ether (150 ml) and the phases were separated. The organic phase was extracted once more with water (100 ml) and the combined aqueous phases were acidified to pH 2 and extracted with ether (100 ml). The organic phase was dried (MgSO$_4$), evaporated and the product was purified by preparative HPLC.

Yield: 315 mg (31%)

$^1$H NMR (DMSO): 7.03 (s, 1H), 3.18–3.58 (m, 24H), 1.95–2.30 (m, 24 H) 0.96–1.09 (m, 108H).

EXAMPLE 7

Tris(8-carboxy-2,2,6,6-tetra-(hydroxyethyl)benzo[1,2-d:4,5-d']bis(1,3)dithiole-4-yl)methyl sodium salt.

To a solution of trifluoromethane sulphonic acid (8.48 ml) in acetonitrile (64.0 ml) and dichloromethane (50.0 ml) at ambient temperature was added a solution of tris(B-hydroxycarbonyl-2,2,6,6-tetra-(t-butoxyethyl)benzo[1,2-d:4,5-d']bis(1,3)dithiole-4-yl)methanol (300 mg, 0.15 mmol) in acetonitrile (8.0 ml) and dichloromethane (8.0 ml). The mixture was stirred for 7 minutes and a 26 mM solution of tin chloride (5.2 ml, 0.14 mmol) was added After 4 minutes ice cold 1 M aqueous sodium hydroxide (96 ml) was added and the phases were separated and the aqueous phase containing the product was collected. The pH was adjusted to pH 2 and the solution was subjected to preparative HPLC. The collected fractions was evaporated to eliminate acetonitrile and the aqueous solution was poured on a pad packed with C-18 material. The pad was washed with deionized water and the product was eluted with ethanol and evaporated to dryness. To the residue was added water (5 ml) and the pH was carefully adjusted to pH 7 with diluted hydrochloric acid and the mixture was lyophilized.

Yield: 37.6 mg (18%)

ESR (1.0 mM in H$_2$O, 100 G): singlet, linewidth 160 mG.

We claim:

1. A radical compound of formula I

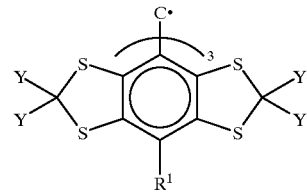

(wherein:

R$^1$ represents a hydrogen atom or group of formula M, —XM, —X—Ar$^2$ or —Ar$^2$;

M represents a water solubilising group;

X represents an oxygen or sulphur atom or a group CO or S(O)$_m$ (where m is 1 to 3);

Ar$^2$ represents a 5 to 10 membered aromatic ring optionally substituted by a water solubilising group M; and each group Y is a hydroxyethyl group) or a deuterated analog, precursor or salt thereof.

2. A radical compound as claimed in claim 1 being

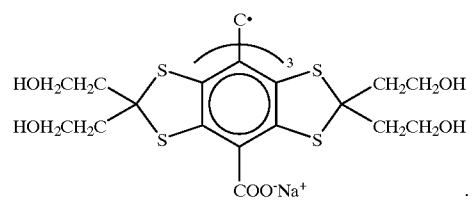

3. A magnetic resonance imaging contrast medium comprising a radical compound as claimed in claim 1 together with at least one pharmacologically acceptable carrier or excipient.

* * * * *

UNITED STATES PATENT AND TRADEMARK OFFICE
CERTIFICATE OF CORRECTION

PATENT NO.    :   6,013,810
DATED         :   January 11, 2000
INVENTOR(S)   :   Mikkel Thaning and Göran Pettersson It is certified that error appears in the above-indentified patent and that said Letters Patent is hereby corrected as shown below:

Title Page: Item [75] under the heading "Inventor"

the below named individual should be included as a co-inventor:

--Göran Pettersson, Hjärup, Sweden--

Signed and Sealed this

Seventh Day of November, 2000

Attest:

Q. TODD DICKINSON

Attesting Officer    Director of Patents and Trademarks